United States Patent
Ahmad et al.

(10) Patent No.: US 9,962,095 B2
(45) Date of Patent: May 8, 2018

(54) OPTICAL HEARTRATE TRACKING

(71) Applicant: Microsoft Technology Licensing, LLC, Redmond, WA (US)

(72) Inventors: Anis Ahmad, Kirkland, WA (US); Ben Walker, Redmond, WA (US); Daniel Kennett, Bellevue, WA (US); Andrew Flavell, Medina, WA (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 455 days.

(21) Appl. No.: 13/869,016

(22) Filed: Apr. 23, 2013

(65) Prior Publication Data

US 2014/0316293 A1 Oct. 23, 2014

(51) Int. Cl.
*A61B 5/024* (2006.01)
*A61B 5/00* (2006.01)

(52) U.S. Cl.
CPC ........... *A61B 5/024* (2013.01); *A61B 5/0077* (2013.01); *A61B 5/02416* (2013.01); *A61B 5/725* (2013.01); *A61B 5/7207* (2013.01); *A61B 5/6887* (2013.01); *A61B 5/7257* (2013.01)

(58) Field of Classification Search
CPC ..... A61B 5/004; A61B 5/0064; A61B 5/0086; A61B 5/02416; G06T 2207/30076; G06T 7/0012
USPC ........................................................ 600/508
See application file for complete search history.

(56) References Cited

U.S. PATENT DOCUMENTS

| | | | | |
|---|---|---|---|---|
| 5,853,364 | A * | 12/1998 | Baker et al. | 600/300 |
| 2007/0266959 | A1 | 11/2007 | Brooks | |
| 2009/0141124 | A1 | 6/2009 | Liu et al. | |
| 2009/0261979 | A1 * | 10/2009 | Breed et al. | 340/576 |
| 2011/0152637 | A1 * | 6/2011 | Kateraas et al. | 600/301 |
| 2011/0251021 | A1 | 10/2011 | Zavadsky et al. | |

(Continued)

FOREIGN PATENT DOCUMENTS

| | | |
|---|---|---|
| WO | 2011042839 A1 | 4/2011 |
| WO | 2013017976 A1 | 2/2013 |
| WO | 2013027141 A2 | 2/2013 |

OTHER PUBLICATIONS

Poh, et al., "Non-Contact, Automated Cardiac Pulse Measurements using Video Imaging and Blind", In Journal of Optics Express, vol. 18, Issue 10, May 7, 2010, 14 pages.

(Continued)

*Primary Examiner* — Amanda Patton
(74) *Attorney, Agent, or Firm* — Mark K. Young; Mayer & Williams PC (57) ABSTRACT

Heartrate tracking is performed entirely optically without the subject being required to wear any monitoring equipment by processing a combination of signals representing frames of video of the sinusoidal motion of a subject's facial skin color changes captured by both IR and visible light (e.g., RGB—red/green/blue) cameras. The IR and RGB graphs that result from the processing are perfectly phase-shifted so that when the IR signal is going down in amplitude, the RGB signal is going up. Such phase-shifting enables the optical heartrate tracking to utilize diverse input feeds so that a tracked signal is accepted as the user's true heartrate when both IR and RGB signals are well correlated.

9 Claims, 10 Drawing Sheets

(56) References Cited

U.S. PATENT DOCUMENTS

2013/0077823 A1    3/2013   Mestha et al.
2013/0296660 A1*   11/2013  Tsien et al. .................. 600/301

OTHER PUBLICATIONS

Sahindrakar, Pratik, "Improving Motion Robustness of Contact-less Monitoring of Heart Rate Using Video Analysis", In Department of Mathematics and Computer Science, University of Technology, Aug. 24, 2011, 58 pages.

Jawahar, Yousuf, "Design of an Infrared based Blood Oxygen Saturation and Heart Rate Monitoring Device", Electrical and Biomedical Engineering Project Report—Submitted in Partial Fulfillment of the requirements for the Degree of Bachelor of Engineering, Apr. 10, 2009, 69 pages.

"Cardioo: Heart Rate Monitoring Made Easy", Retrieved on: Apr. 4, 2013, Available at: http://cardiio.com/ (3 pages total).

"iTunes Preview", Retrieved on: Apr. 4, 2013, Available at: https://itunes.apple.com/ca/app/vital-signs-camera-philips/id474433446 (2 pages total).

Honig, Zach, "Fujitsu Software Uses a Smartphone's Camera to Measure Your Pulse", Published on: Mar. 18, 2013, (8 pages total) Available at: http://www.engadget.com/2013/03/18/fujitsu-pulse-software/.

"Making the Invisible Visible in Video", Published on: Jul. 16, 2012, (2 pages total) Available at: http://www.youtube.com/watch?v=sVIC_-e-4yg .

"Optics InfoBase", Retrieved on: Apr. 4, 2013, (7 pages total) Available at: http://www.opticsinfobase.org/view_article.cfm?gotourl=http%3A%2F%2Fwww%2Eopticsinfobase%2Eorg%2FDirectPDFAccess%2FFDCE083A%2D9D1B%2D4E17%2D7FB5394AE423258D%5F199381%2Foe%2D18%2D10%2D10762%2Epdf%3Fda%3D1%026id%3D199381%26seq%3D0%26mobile%3Dno&org.

Haji Mohd, et al., "Effective Geometric Calibration and Facial Feature Extraction Using Multi Sensors", In International Journal of Engineering Science and Innovative Technology, vol. 1, Issue 2, Nov. 2012, 9 pages.

"International Search Report & Written Opinion for PCT Patent Application No. PCT/US2014/034742", dated Jun. 27, 2014, (11 Pages total).

Sun, et al., "Motion-Compensated Non-contact Imaging Photoplethysmography to Monitor Cardiorespiratory Status during Exercise", In Journal of Biomedical Optics, vol. 16, Issue 7, Jul. 18, 2011, (10 Pages total).

"International Preliminary Report on Patentabilty for PCT Patent Application No. PCT/US2014/034742", dated Nov. 5, 2015, (8 Pages total).

"Office Action and Search Report Issued in Taiwan Patent Application No. 103114291", dated Jun. 8, 2017, (15 Pages total).

* cited by examiner

OPTICAL HEARTRATE TRACKING

BACKGROUND

Optical heartrate monitoring systems typically use an optical radiation sensor that is sensitive to visible or infrared (IR) light to detect the flow of hemoglobin in blood in the human body. In some systems, a subject wears some form of monitoring equipment or a sensor is positioned to contact an extremity such as a finger or earlobe. Other non-contact optical heartrate monitoring systems detect hemoglobin flow by measuring brightness variations in a subject's face. While existing systems can perform satisfactorily in many situations, they are not generally well adapted for usage scenarios in which the subject is expected to be active. For example, contact systems can often be cumbersome and impractical for application to athletes and fitness enthusiasts, and also ambulatory medical patients, while non-contact systems typically require the subject to remain still as the heartrate monitoring is performed.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Heartrate tracking is performed entirely optically without the subject being required to wear any monitoring equipment by processing a combination of signals representing frames of video of the sinusoidal motion of a subject's facial skin color changes captured by both IR and visible light (e.g., RGB—red/green/blue) cameras. The IR and RGB graphs that result from the processing are perfectly phase-shifted so that when the IR signal is going down in amplitude, the RGB signal is going up. Such phase-shifting enables the optical heartrate tracking to utilize diverse input feeds so that a tracked signal is accepted as the user's true heartrate when both IR and RGB signals are well correlated.

In various illustrative examples, a heartrate tracking engine executing on a computing platform, such as a gaming or multimedia console having calibrated IR and RGB video cameras, is arranged to support a number of processing pipelines that process the captured IR and RGB video frames into a final frequency-space graph that includes a well-defined peak amplitude that defines the subject's heartrate signal. A face alignment and preparation pipeline processes the IR and RGB frames from multiple channels to generate a decomposed (i.e., being incorporated to a single signal measurement in one channel), frame-aligned, facial skin-only signal that removes the effects of eyelid, mouth, and hair motion that would otherwise corrupt the signal integrity. A signal-finding pipeline generates a time-space graph from decomposed, frame-aligned, facial skin-only signal. A signal-extracting pipeline processes the time-space graphs into frequency-space graphs for the IR and RGB frames and applies time-space and frequency-space smoothing methods to produce a best-effort estimate of the subject's heartrate. A heartrate identification pipeline buckets the highest peaks in the merged frequency-space graphs over multiple frames and generates smoothed curves which are summed to identify a heartrate signal which can be returned to a calling application or operating system that is executing on the computing platform.

Advantageously, the present optical heartrate tracking operates robustly under a variety of light conditions and subject skin pigmentations, over a wide range of distances between the subject and cameras, and with a high tolerance for subject motion. The optical heartrate tracking is thus well adapted to a variety of applications in which the subject is active including gaming, fitness, and other scenarios.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

It should be appreciated that the above-described subject matter may be implemented as a computer-controlled apparatus, a computer process, a computing system, or as an article of manufacture such as one or more computer-readable storage media. These and various other features will be apparent from a reading of the following Detailed Description and a review of the associated drawings.

DETAILED DESCRIPTION

The present optical heartrate tracking makes use of the observations that blood pumped from the heart contains oxygenated hemoglobin ($HbO_2$). As oxygen is absorbed by the body, the hemoglobin becomes de-oxygenated (Hb). Oxygenated hemoglobin and de-oxygenated hemoglobin reflect different wavelengths of light differently. Oxygenated hemoglobin strongly reflects red light while de-oxygenated hemoglobin reflects blue light. By tracking the sinusoidal motion of human skin color caused by oxygenated blood flooding in via heartbeat, the oxygen being consumed, then more oxygenated blood flooding in from the next heartbeat, a person's heartrate can be determined. The present optical heartrate tracking may use IR and visible light RGB (red/ green/blue) cameras to maintain two signals on the subject's skin, and weight the resulting signals from each camera as needed to achieve optimal results. In particular, frames captured by the RGB camera are processed to measure heartrate using visible light wavelengths (400-720 nm), while IR frames within a range of IR wavelengths above 800 nm are processed. For visible wavelengths, $HbO_2$ is more reflective than Hb and for IR wavelengths, Hb is more reflective than $HbO_2$.

Figure 1:
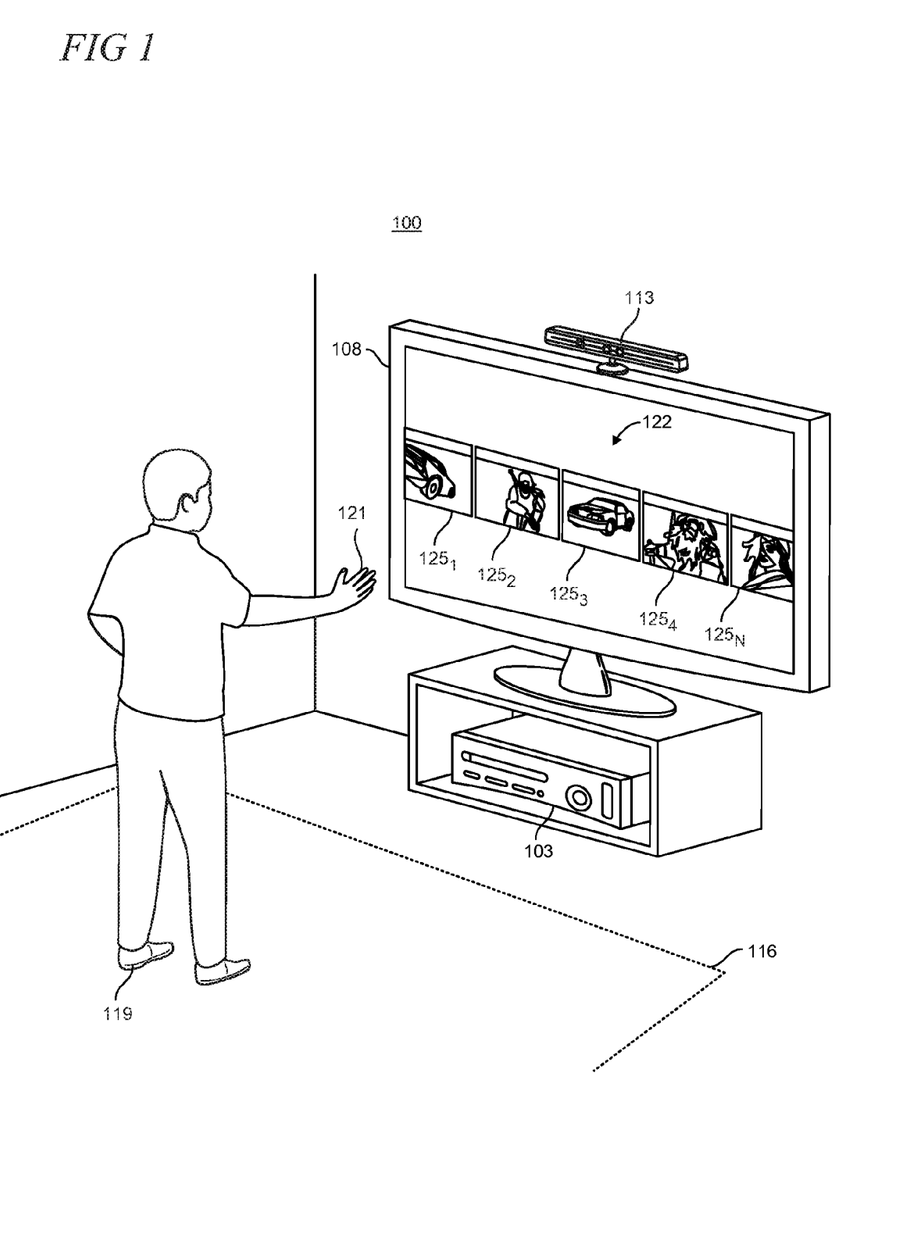
FIGS. 1 and 2 show an illustrative computing environment in which the present optical heartrate tracking may be implemented.

Turning to the drawings, FIG. 1 shows an illustrative computing environment 100 in which the present optical heartrate tracking may be implemented. It is emphasized that the environment 100 is intended to be illustrative and that other environments which include other types of devices, applications, and usage scenarios may also be able to utilize the principles described herein. The environment 100 includes a computing platform such as multimedia console 103 that is typically configured for running gaming and non-gaming applications using local and/or networked programming and content, playing pre-recorded multimedia such as optical discs including DVDs (Digital Versatile Discs) and CDs (Compact Discs), streaming multimedia from a network, participating in social media, browsing the Internet and other networked media and content, or the like using a coupled audio/visual display 108, such as a television.

The multimedia console 103 in this example is operatively coupled to a capture device 113 which may be implemented using one or more video cameras that are configured to visually monitor a physical space 116 (indicated generally by the dashed line in FIG. 1) that is occupied by a user 119. As described below in more detail, the capture device 113 is configured to capture, track, and analyze the movements and/or gestures of the user 119 so that they can be used as controls that may be employed to affect, for example, an application or an operating system running on the multimedia console 103. Various motions of the hands 121 or other body parts of the user 119 may correspond to common system wide tasks such as selecting a game or other application from a main user interface.

For example as shown in FIG. 1, the user 119 can navigate among selectable objects 122 that include various icons $125_{1-N}$ that are shown on the coupled display 108, browse through items in a hierarchical menu, open a file, close a file, save a file, or the like. In addition, the user 119 may use movements and/or gestures to end, pause, or save a game, select a level, view high scores, communicate with a friend, etc. Virtually any controllable aspect of an operating system and/or application may be controlled by movements of the user 119. A full range of motion of the user 119 may be available, used, and analyzed in any suitable manner to interact with an application or operating system that executes in the environment 100.

Figure 2:
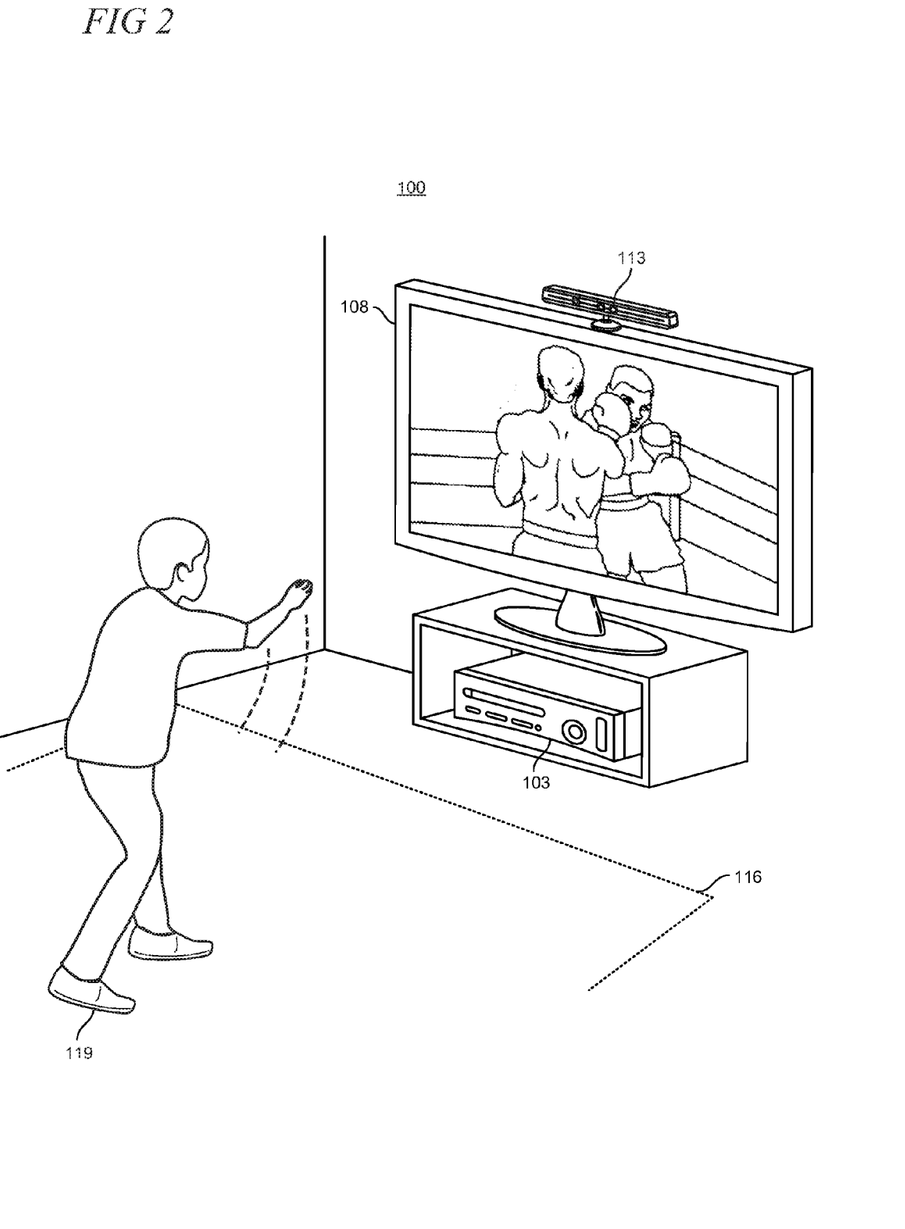

The capture device 113 can also be utilized to capture, track, and analyze movements by the user 119 to control gameplay as a gaming application executes on the multimedia console 103. For example, as shown in FIG. 2, a gaming application such as a boxing game uses the display 108 to provide a visual representation of a boxing opponent to the user 119 as well as a visual representation of a player avatar that the user 119 may control with his or her movements. The user 119 may make movements (e.g., throwing a punch) in the physical space 116 to cause the player avatar to make a corresponding movement in the game space. Movements of the user 119 may be recognized and analyzed in the physical space 116 such that corresponding movements for game control of the player avatar in the game space are performed.

Gaming applications supported by the multimedia console 103 provide an exemplary context in which the present optical heartrate tracking may be advantageously utilized. For example, in the boxing game discussed above, a game designer may wish to add a game feature in which a user's heartrate is monitored along with other factors (such as number of punches thrown and landed per round) as an indication of the user's performance, skill, or fitness level. It will be further appreciated that heartrate tracking may be useful in other contexts including both gaming and non-gaming contexts.

Figure 3:
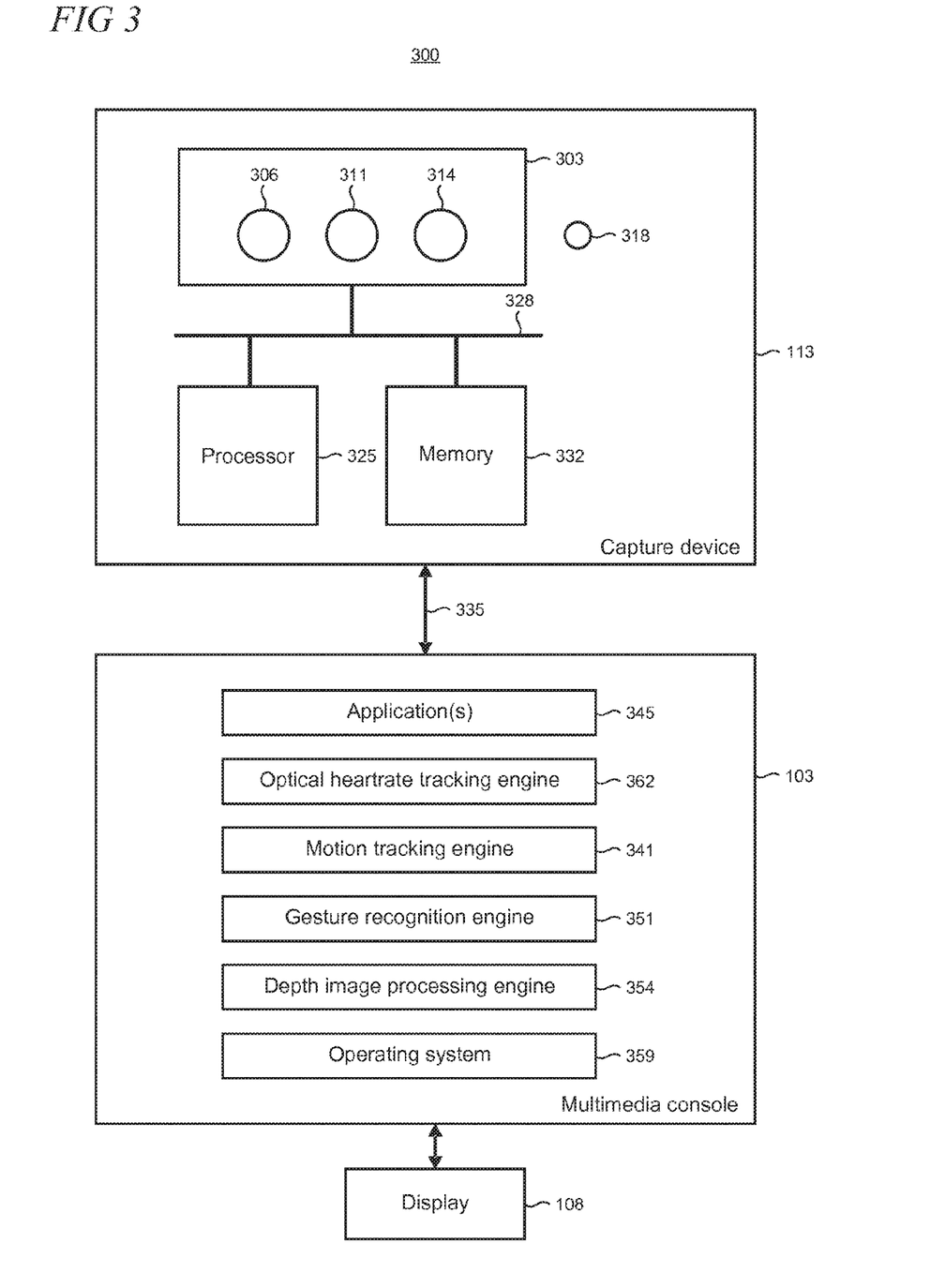
FIG. 3 shows an illustrative capture device that may be used in part to implement the present optical heartrate tracking.

FIG. 3 shows illustrative functional components of the capture device 113 that may be used as part of a target recognition, analysis, and tracking system 300 to recognize human and non-human targets in a capture area of the physical space 116 (FIG. 1) without the use of special sensing devices attached to the subjects, uniquely identify them, and track them in three-dimensional space. The capture device 113 may be configured to capture video with depth information including a depth image that may include depth values via any suitable technique including, for example, time-of-flight, structured light, stereo image, or the like. In some implementations, the capture device 113 may organize the calculated depth information into "Z layers," or layers that may be perpendicular to a Z-axis extending from the depth camera along its line of sight.

As shown in FIG. 3, the capture device 113 includes an image camera component 303. The image camera component 303 may be configured to operate as a depth camera that may capture a depth image of a scene. The depth image may include a two-dimensional (2D) pixel area of the captured scene where each pixel in the 2D pixel area may represent a depth value such as a distance in, for example, centimeters, millimeters, or the like of an object in the captured scene from the camera. In this example, the image camera component 303 includes an IR light component 306, an IR camera 311, and a visible light RGB camera 314.

Various techniques may be utilized to capture depth video frames. For example, in time-of-flight analysis, the IR light component 306 of the capture device 113 may emit an infrared light onto the capture area and may then detect the backscattered light from the surface of one or more targets and objects in the capture area using, for example, the IR camera 311 and/or the RGB camera 314. In some embodiments, pulsed infrared light may be used such that the time between an outgoing light pulse and a corresponding incoming light pulse may be measured and used to determine a physical distance from the capture device 113 to a particular location on the targets or objects in the capture area. Additionally, the phase of the outgoing light wave may be compared to the phase of the incoming light wave to determine a phase shift. The phase shift may then be used to determine a physical distance from the capture device to a particular location on the targets or objects. Time-of-flight analysis may be used to indirectly determine a physical distance from the capture device 113 to a particular location on the targets or objects by analyzing the intensity of the reflected beam of light over time via various techniques including, for example, shuttered light pulse imaging.

In other implementations, the capture device 113 may use structured light to capture depth information. In such an analysis, patterned light (i.e., light displayed as a known pattern such as a grid pattern or a stripe pattern) may be projected onto the capture area via, for example, the IR light component 306. Upon striking the surface of one or more targets or objects in the capture area, the pattern may become deformed in response. Such a deformation of the pattern may be captured by, for example, by the IR camera 311 and/or the RGB camera 314 and may then be analyzed to determine a physical distance from the capture device to a particular location on the targets or objects.

The capture device 113 may utilize two or more physically separated cameras that may view a capture area from different angles, to obtain visual stereo data that may be resolved to generate depth information. Other types of depth image arrangements using single or multiple cameras can also be used to create a depth image. The capture device 113 may further include a microphone 318. The microphone 318 may include a transducer or sensor that may receive and convert sound into an electrical signal. The microphone 318 may be used to reduce feedback between the capture device 113 and the multimedia console 103 in the target recognition, analysis, and tracking system 300. Additionally, the microphone 318 may be used to receive audio signals that may also be provided by the user 119 to control applications such as game applications, non-game applications, or the like that may be executed by the multimedia console 103.

The capture device 113 may further include a processor 325 that may be in operative communication with the image camera component 303 over a bus 328. The processor 325 may include a standardized processor, a specialized processor, a microprocessor, or the like that may execute instructions that may include instructions for storing profiles, receiving the depth image, determining whether a suitable target may be included in the depth image, converting the suitable target into a skeletal representation or model of the target, or any other suitable instruction. The capture device 113 may further include a memory component 332 that may store the instructions that may be executed by the processor 325, images or frames of images captured by the cameras, user profiles or any other suitable information, images, or the like. According to one example, the memory component 332 may include random access memory (RAM), read only memory (ROM), cache, Flash memory, a hard disk, or any other suitable storage component. As shown in FIG. 3, the memory component 332 may be a separate component in communication with the image capture component 303 and the processor 325. Alternatively, the memory component 332 may be integrated into the processor 325 and/or the image capture component 303. In one embodiment, some or all of the components 303, 306, 311, 314, 318, 325, 328, and 332 of the capture device 113 are located in a single housing.

The capture device 113 operatively communicates with the multimedia console 103 over a communication link 335. The communication link 335 may be a wired connection including, for example, a USB (Universal Serial Bus) connection, a Firewire connection, an Ethernet cable connection, or the like and/or a wireless connection such as a wireless 802.11 connection. The multimedia console 103 can provide a clock to the capture device 113 that may be used to determine when to capture, for example, a scene via the communication link 335. The capture device 113 may provide the depth information and images captured by, for example, the IR camera 311 and/or the RGB camera 314, including a skeletal model and/or facial tracking model that may be generated by the capture device 113, to the multimedia console 103 via the communication link 335. The multimedia console 103 may then use the skeletal and/or facial tracking models, depth information, and captured images to, for example, create a virtual screen, adapt the user interface, and control an application.

A motion tracking engine 341 uses the skeletal and/or facial tracking models and the depth information to provide a control output to one more applications (representatively indicated by an application 345 in FIG. 3) running on the multimedia console 103 to which the capture device 113 is coupled. The information may also be used by a gesture recognition engine 351, depth image processing engine 354, operating system 359, and/or optical heartrate tracking engine 362. The depth image processing engine 354 uses the depth images to track motion of objects, such as the user and other objects. The depth image processing engine 354 will typically report to operating system 359 an identification of each object detected and the location of the object for each frame. The operating system 359 can use that information to update the position or movement of an avatar, for example, or other images shown on the display 108, or to perform an action on the user interface.

The gesture recognition engine 351 may utilize a gestures library (not shown) that can include a collection of gesture filters, each comprising information concerning a gesture that may be performed, for example, by a skeletal model (as the user moves). The gesture recognition engine 351 may compare the frames captured by the capture device 113 in the form of the skeletal model and movements associated with it to the gesture filters in the gesture library to identify when a user (as represented by the skeletal model) has performed one or more gestures. Those gestures may be associated with various controls of an application. Thus, the multimedia console 103 may employ the gestures library to interpret movements of the skeletal model and to control an operating system or an application running on the multimedia console based on the movements.

Figure 4:
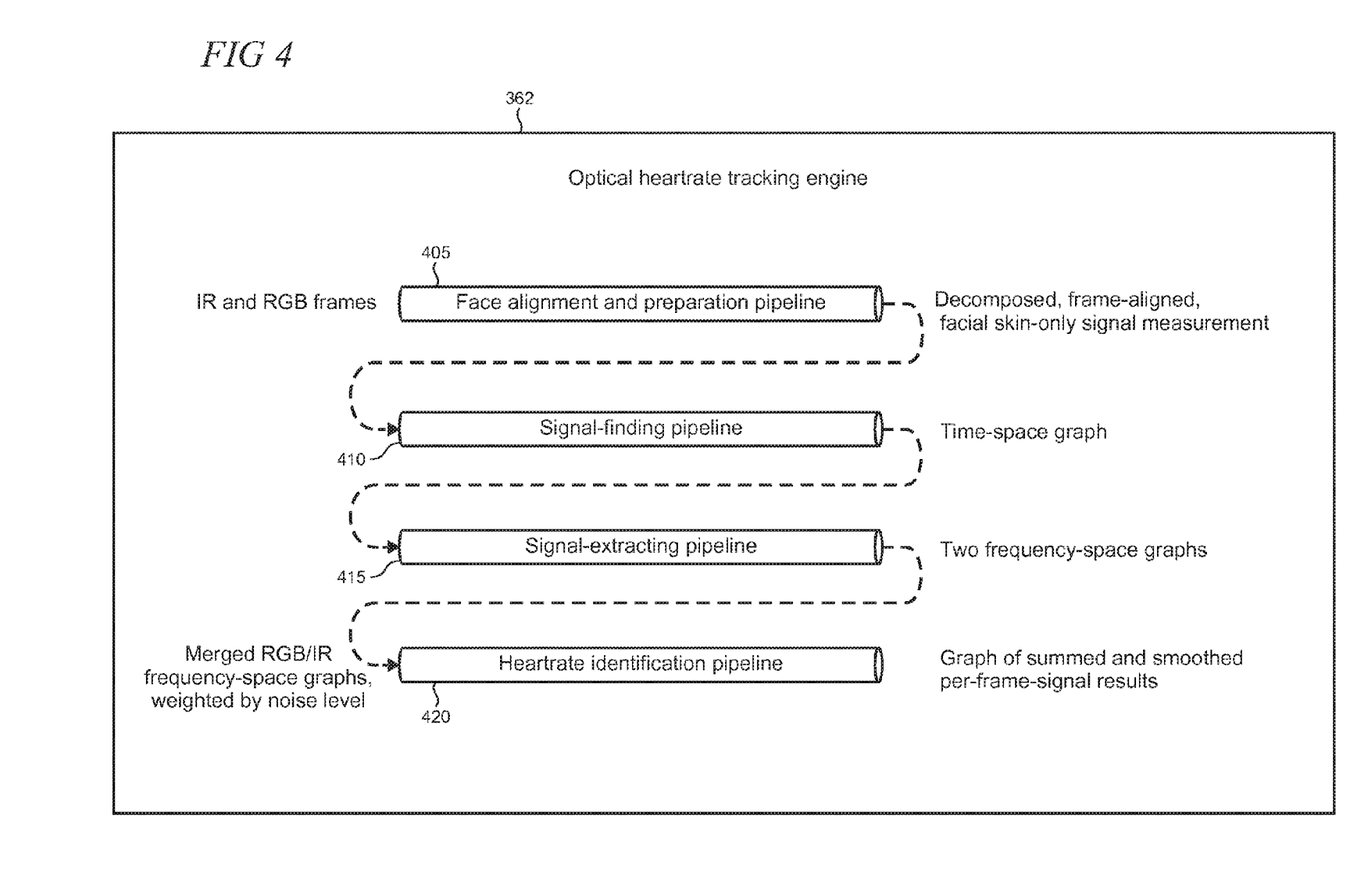
FIG. 4 shows illustrative processing pipelines that are supported by an optical heartrate tracking engine.

FIG. 4 shows functional details of the optical heartrate tracking engine 362. In particular, the optical heartrate tracking engine 362 can utilize a number of processing pipelines including a face alignment and preparation pipeline 405, a signal-finding pipeline 410, a signal-extracting pipeline 415, and a heartrate identification pipeline 420. As shown, the processing pipelines are arranged sequentially so that the output of one processing pipeline provides the input to a subsequent processing pipeline. The individual pipelines may be arranged to run in parallel in alternative implementations, for example when the IR and RGB cameras operate at different framerates.

The input to the optical heartrate tracking engine 362 typically includes both IR and RGB frames that are captured by the capture device 113 and passed to the engine 362 via the operating system 359 or application 345 depending on the requirements of a given implementation. The output of the optical heartrate tracking engine 362 is a frequency-space graph that includes an identified heartrate signal which can be returned to a calling application, operating system, or other component supported by the multimedia console 103.

Figure 5:
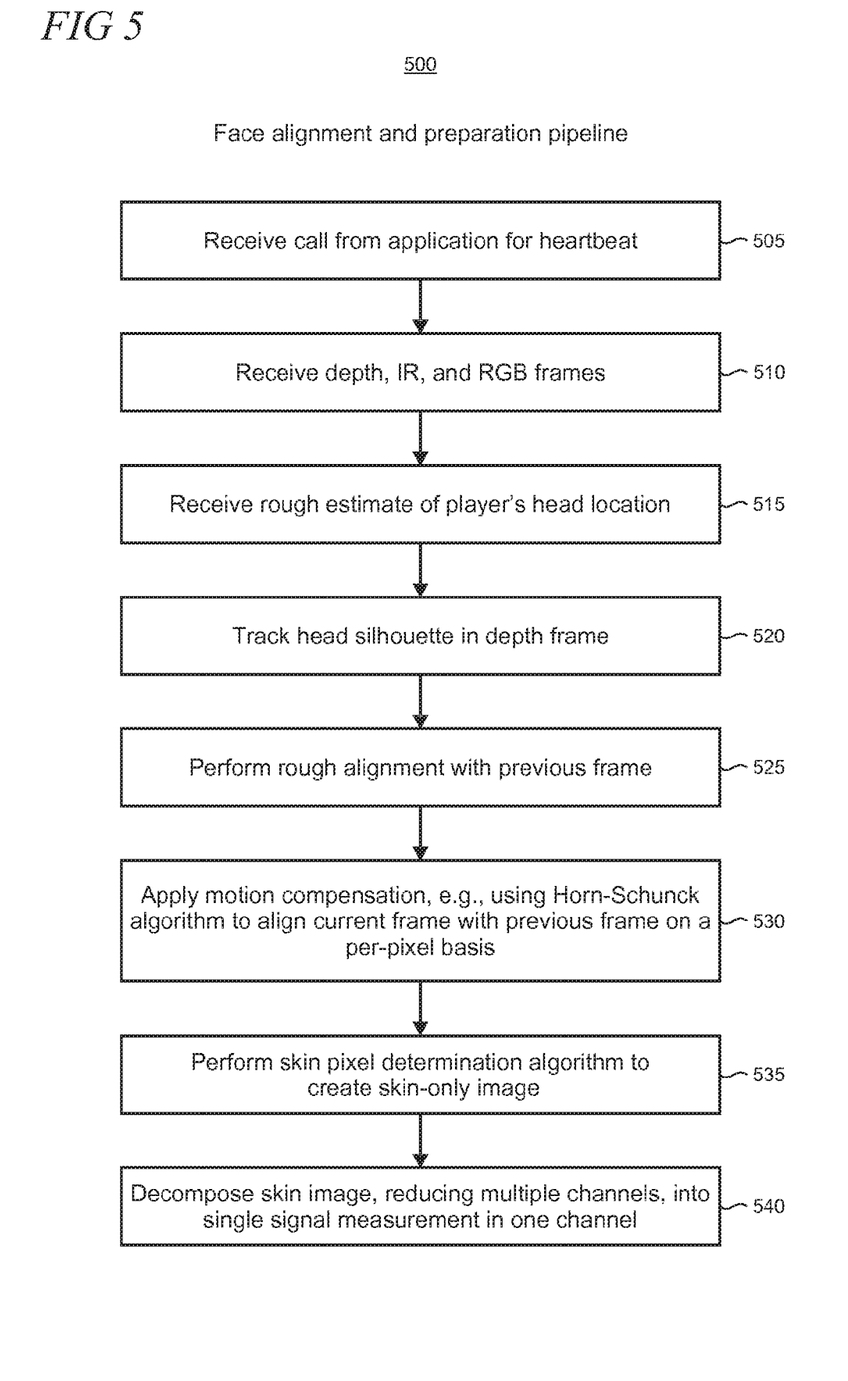
FIG. 5 shows a flowchart of an illustrative method implemented by a face alignment and preparation pipeline.

The face alignment and preparation pipeline 405 can implement the method 500 shown in the flowchart of FIG. 5. Unless specifically stated, the methods or steps in the flowchart of FIG. 5 and those in the other flowcharts shown in the drawings and described below are not constrained to a particular order or sequence. In addition, some of the methods or steps thereof can occur or be performed concurrently and not all the methods or steps have to be performed in a given implementation depending on the requirements of such implementation and some methods or steps may be optionally utilized. For example, additional signal filtering may be desired in some scenarios to improve noise performance in certain operating environments at the expense of increased computational and system resource usage. Likewise, some steps may be eliminated in some applications to reduce overhead while decreasing robustness or motion tolerance, for example. The various feature, cost, overhead, performance, and robustness tradeoffs which may be implemented in any given application may typically be viewed as a matter of design choice. Responsively to a call from an application (or operating system or other component) for the user's heartbeat (as indicated by reference numeral 505), the pipeline 405 receives depth, IR, and RGB frames (510). The face alignment and preparation pipeline 405 receives a rough estimate of the user's head location in the physical space 116 (FIG. 1) obtained from the motion tracking engine 341 (FIG. 3) which could employ, for example, either skeletal or facial tracking (515).

Using the received rough estimate of the user's head location, the head silhouette is tracked in the depth frame (520) so that the head is clearly separated from background, and a rough alignment with the head location from the previous frame is performed (525). Optical flow-based motion compensation, for example using the Horn-Schunck algorithm, is performed to per-pixel align the current frame with the previous frame (530). This preserves broad details of the frame but warps changes like raised eyebrows, moving mouth, etc. in the facial image to align them with the previous frame. In the event that motion blur proves to be a significant source of noise, various de-blur/de-ghosting techniques may be optionally implemented to reduce its impact.

A skin pixel determination algorithm is utilized to create a skin-only image (535). In this illustrative example, the skin pixel determination algorithm is internally generated and machine-learned that determines which pixels are likely skin pixels and removes pixels that are associated with hair, eyes, mouth, and nostrils. Without this step, noise from blinking eyes or moving mouth and hair can typically be expected to corrupt the heartbeat tracking results. The resulting frame-aligned skin-only image is decomposed so that all the image pixels from the IR and RGB frames in multiple channels are incorporated into a single signal measurement in one channel (540).

Figure 6:
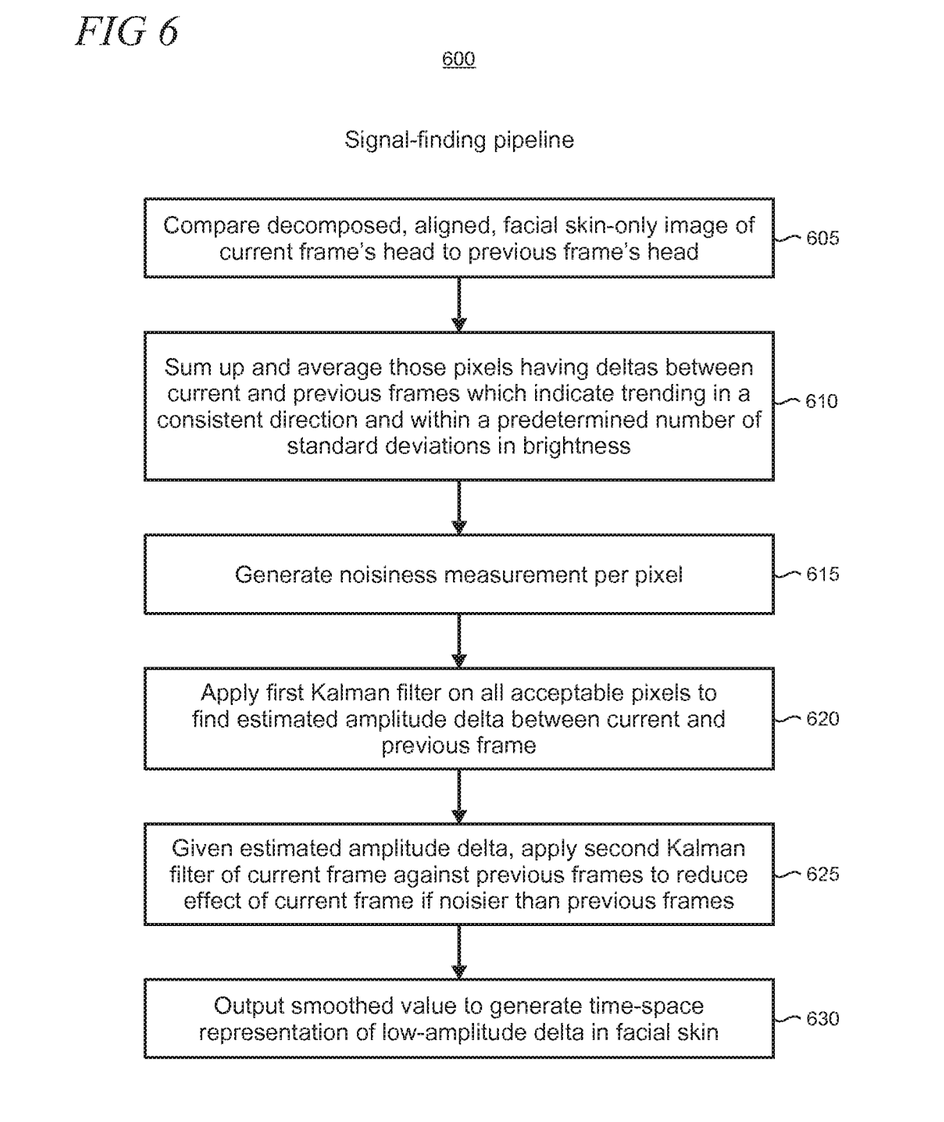
FIG. 6 shows a flowchart of an illustrative method implemented by a signal-finding pipeline.

The signal-finding pipeline 410 can implement the method 600 shown in the flowchart of FIG. 6. A per-pixel comparison of the decomposed, aligned, skin-only image of the current frame's head is performed against a cached decomposed version of the previous frame's head (605). Those pixels having deltas between the previous frame's head and current frame's head which are determined to be trending in a consistent direction, and are within a given number of standard deviations in brightness, are summed up and averaged (610). The pixels meeting these criteria are termed "acceptable pixels." A measure of noisiness of per-pixel is generated based on how far the pixel is from the average for delta and brightness (615).

A first Kalman filter may be applied to an array which includes all acceptable pixels, averaging each pixel's delta between frames, weighted by the pixel likeliness of being noise, to find an estimated amplitude delta in the time between the two frames (620). Thus, the application of the first Kalman filter enables a determination to be made as to whether the level of reflectivity in the pixels is increasing, decreasing, or remaining the same. It is emphasized that the utilization of Kalman filters is intended to be illustrative and that other known types of filters can also be applied depending on the needs of a particular implementation of heartrate tracking A second Kalman filter may be applied to the output from the first Kalman filter (625). That is, given the estimated amplitude delta, a filter of the current frame is applied against previous frames to reduce the impact on the heartbeat signal if the current frame is noisier than most frames. The second Kalman filter additionally notes the time each measurement was generated and outputs a smoothed value that takes into account both the likelihood-of-noise per measurement and how long ago that measurement was performed in recognition that the current frame measurement is more likely to be similar to measurements from one or two frames ago, for example, than from eight or nine frames ago. Accordingly, the first Kalman filter may be viewed as removing noise across measurements for a given timeslice, while the second Kalman filter removes noise across timeslices for the final heartbeat signal.

As an illustrative example of the interactions between the two Kalman filters, say the user 119 (FIG. 1) turns off the lights in the physical space 116 between two successive frames which results in the second frame being 50% darker than the first frame. The first Kalman filter would reduce the impact of pixels that are noisy beyond the 50% change in brightness from turning the lights off, and it would find that there is an average delta between frames of 50% and that the measurement is very noisy. The second Kalman filter receives this 50%/very noisy data point and, provided that previous frame measurements were not as noisy, the second Kalman filter would use those previous measurements in the place of this noisy data point to generate a per-frame delta for this frame.

The output of the second Kalman filter over time is utilized to create a time-space representation of low-amplitude deltas in facial skin (630 in FIG. 6). The principal source of these deltas is heartrate. While the signal-finding pipeline 410 on its own can return a time-space graph that corresponds to heartrate under ideal scenarios, in typical practice, such a time-space graph can be expected to be heavily corrupted by noise. The signal-extracting pipeline 415 subjects the noise-corrupted time-space graph to additional operations covered by method 700 shown in the flowchart of FIG. 7.

Figure 7:
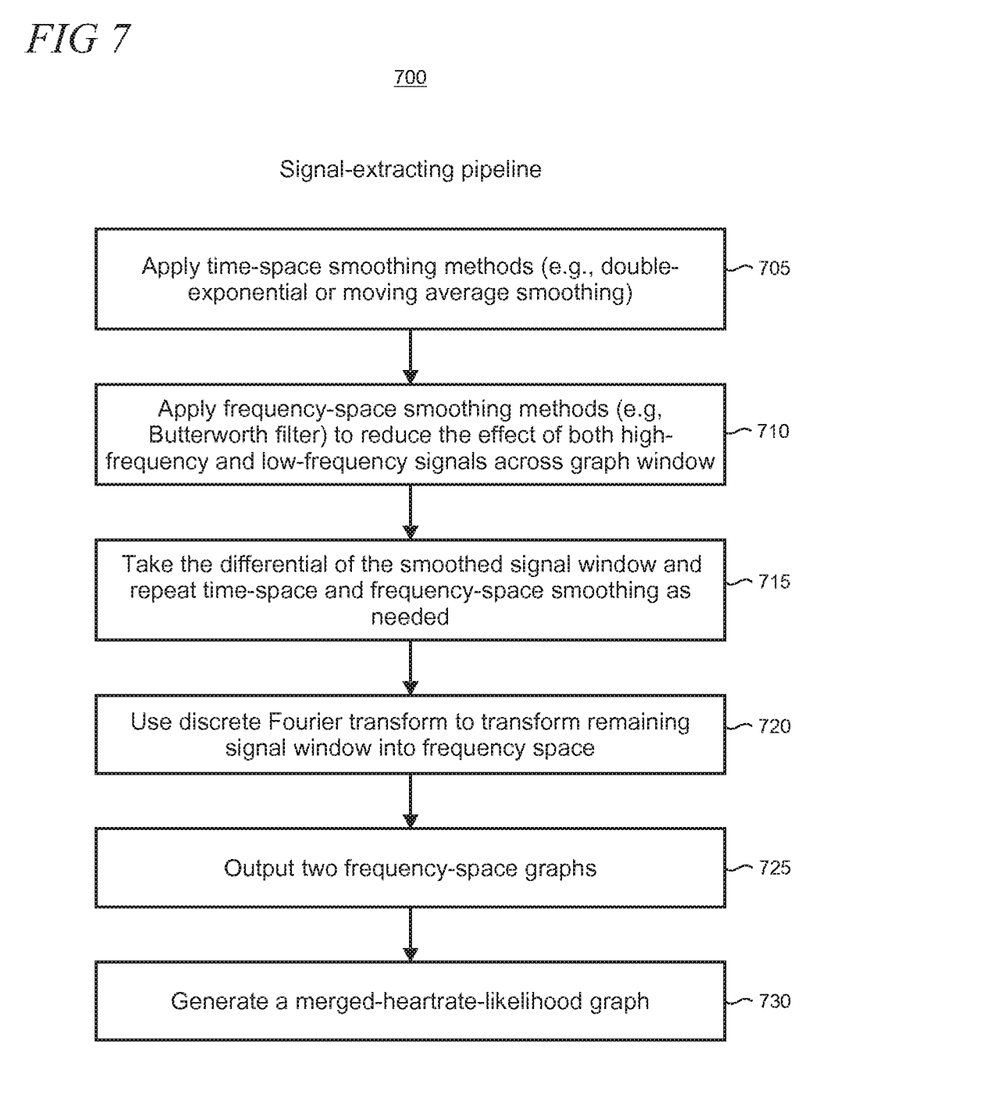
FIG. 7 shows a flowchart of an illustrative method implemented by a signal-extracting pipeline.

In typical implementations, the signal-extracting pipeline 415 runs on a separate thread from the signal-finding pipeline 410 so that the signal-extracting pipeline can process information at 30 fps (frames per second) even in cases where the capture device is not able to reliably provide frames at 30 fps, for example due to resource or other constraints existing at a given time in the environment. Time-space smoothing methods can be applied (705) such as double-exponential or moving-average smoothing, to reduce the impact of high-frequency jitter. Frequency-space smoothing methods such as the Butterworth filter, may be applied (710) to reduce the impact of both high-frequency and low-frequency signals across the graph window. For example, signals below approximately 40 bpm (beats per minute) and above approximately 180 bpm (i.e., 2/3 Hz to 3 Hz) are not likely to be the user's heartrate and may be excluded from the graph window in typical applications.

A differential of the smoothed signal window (which amplifies signal, at the cost of amplifying any remaining noise) is applied and time-space and frequency-space smoothing may be repeated as needed (715). A discrete Fourier transform is then applied to transform the remaining signal window into frequency space (720). The output of the signal-extracting pipeline 415 includes two frequency-space graphs, one for IR and the other for RGB, which represent the engine's best effort estimate of the user's heartrate (725). Ideally, these frequency-space graphs will have one peak, and be entirely flat otherwise, which indicates no signal found at most frequencies while indicating a strong signal at one frequency (i.e., the heartrate). In practice, however, the graphs are still often noisy. A merged-heartrate-likelihood graph is generated that is the average of IR and RGB frequency-space graphs, weighted by each graph's noise level (730).

Figure 8:
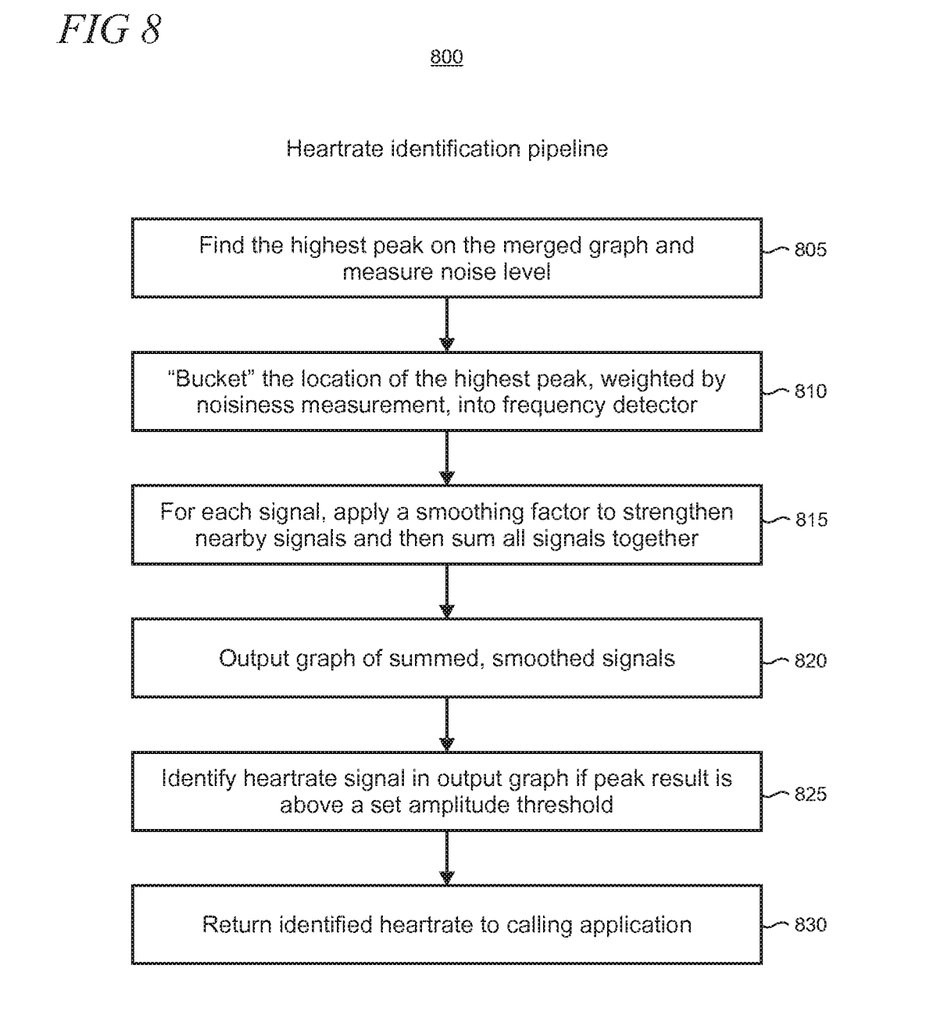
FIG. 8 shows a flowchart of an illustrative method implemented by a heartrate identification pipeline.

The merged RGB/IR frequency-space graph is fed into the heartrate identification pipeline 420 which can perform the method 800 shown in FIG. 8. The pipeline 420 finds the highest peak on the merged RGB/IR frequency-space graph (which represents the signal most likely to be heartrate) and measures its noise level (805). The location of the highest peak, weighted by noisiness measurement, is bucketed into a frequency detector (810). In an illustrative example, the frequency detector may store approximately the past few seconds of frame signals (e.g., five seconds). For each signal, the frequency detector applies a smoothing factor to strengthen the contribution of nearby signals and then sums all the signals together (815). In one illustrative example, a Gaussian is generated having a kernel width of approximately 3 bpm and an amplitude that equals the signal noisiness measurement. The smoothing factor (for example, using the generated Gaussian) is utilized so that signals of 62 bpm and 63 bpm, for example, are not treated as entirely separate.

A graph of the summed, smoothed signals is output (820). A heartrate signal is identified in the output graph if a peak result is above a set threshold amplitude (825) and the identified heartrate is returned to the calling application (830).

Figure 9:
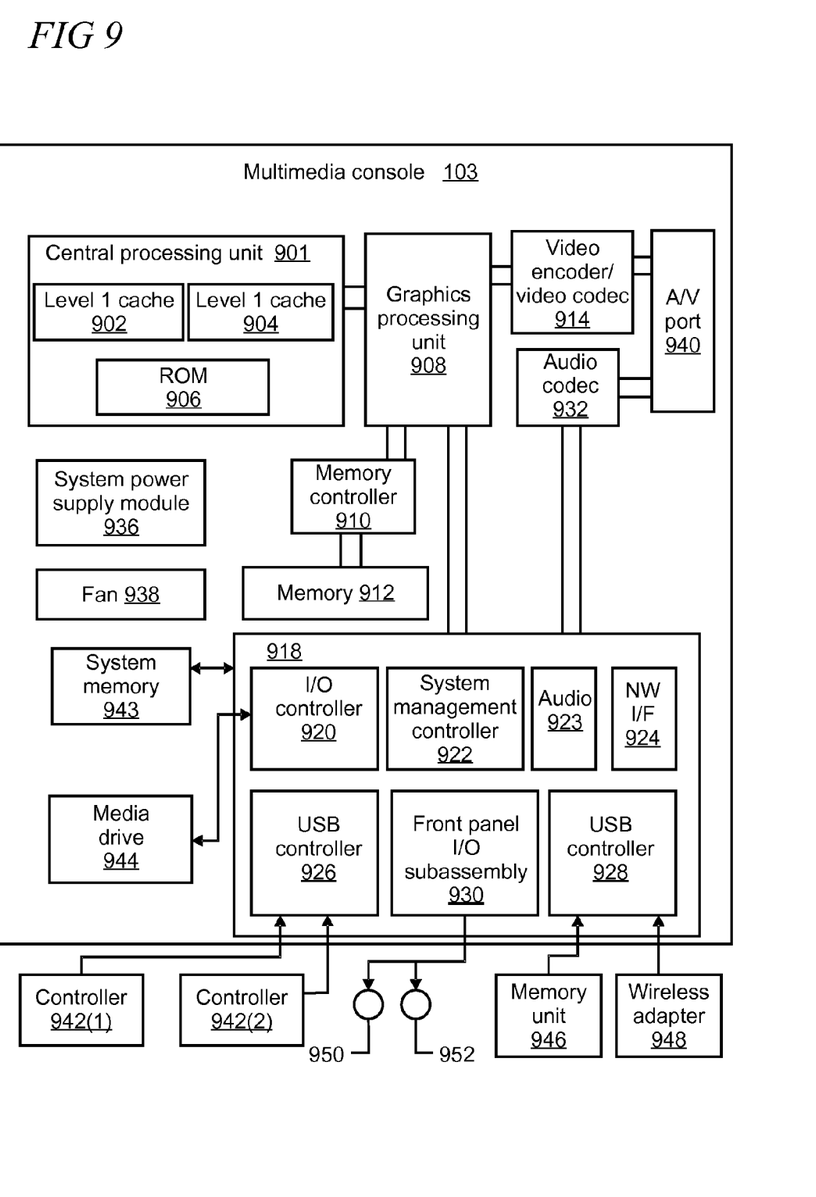
FIG. 9 shows a block diagram of an illustrative multimedia console that may be used in part to implement the present optical heartrate tracking.

FIG. 9 is an illustrative functional block diagram of the multimedia console 103 shown in FIGS. 1-2. As shown in FIG. 9 the multimedia console 103 has a central processing unit (CPU) 901 having a level 1 cache 902, a level 2 cache 904, and a Flash ROM (Read Only Memory) 906. The level 1 cache 902 and the level 2 cache 904 temporarily store data and hence reduce the number of memory access cycles, thereby improving processing speed and throughput. The CPU 901 may be configured with more than one core, and thus, additional level 1 and level 2 caches 902 and 904. The Flash ROM 906 may store executable code that is loaded during an initial phase of a boot process when the multimedia console 103 is powered ON.

A graphics processing unit (GPU) 908 and a video encoder/video codec (coder/decoder) 914 form a video processing pipeline for high speed and high resolution graphics processing. Data is carried from the GPU 908 to the video encoder/video codec 914 via a bus. The video processing pipeline outputs data to an A/V (audio/video) port 940 for transmission to a television or other display. A memory controller 910 is connected to the GPU 908 to facilitate processor access to various types of memory 912, such as, but not limited to, a RAM.

The multimedia console 103 includes an I/O controller 920, a system management controller 922, an audio processing unit 923, a network interface controller 924, a first USB host controller 926, a second USB controller 928, and a front panel I/O subassembly 930 that are preferably implemented on a module 918. The USB controllers 926 and 928 serve as hosts for peripheral controllers 942(1)-942(2), a wireless adapter 948, and an external memory device 946 (e.g., Flash memory, external CD/DVD ROM drive, removable media, etc.). The network interface controller 924 and/or wireless adapter 948 provide access to a network (e.g., the Internet, home network, etc.) and may be any of a wide variety of various wired or wireless adapter components including an Ethernet card, a modem, a Bluetooth module, a cable modem, and the like.

System memory 943 is provided to store application data that is loaded during the boot process. A media drive 944 is provided and may comprise a DVD/CD drive, hard drive, or other removable media drive, etc. The media drive 944 may be internal or external to the multimedia console 103. Application data may be accessed via the media drive 944 for execution, playback, etc. by the multimedia console 103. The media drive 944 is connected to the I/O controller 920 via a bus, such as a Serial ATA bus or other high speed connection (e.g., IEEE 1394).

The system management controller 922 provides a variety of service functions related to assuring availability of the multimedia console 103. The audio processing unit 923 and an audio codec 932 form a corresponding audio processing pipeline with high fidelity and stereo processing. Audio data is carried between the audio processing unit 923 and the audio codec 932 via a communication link. The audio processing pipeline outputs data to the A/V port 940 for reproduction by an external audio player or device having audio capabilities.

The front panel I/O subassembly 930 supports the functionality of the power button 950 and the eject button 952, as well as any LEDs (light emitting diodes) or other indicators exposed on the outer surface of the multimedia console 103. A system power supply module 936 provides power to the components of the multimedia console 103. A fan 938 cools the circuitry within the multimedia console 103.

The CPU 901, GPU 908, memory controller 910, and various other components within the multimedia console 103 are interconnected via one or more buses, including serial and parallel buses, a memory bus, a peripheral bus, and a processor or local bus using any of a variety of bus architectures. By way of example, such architectures can include a Peripheral Component Interconnects (PCI) bus, PCI-Express bus, etc.

When the multimedia console 103 is powered ON, application data may be loaded from the system memory 943 into memory 912 and/or caches 902 and 904 and executed on the CPU 901. The application may present a graphical user interface that provides a consistent user experience when navigating to different media types available on the multimedia console 103. In operation, applications and/or other media contained within the media drive 944 may be launched or played from the media drive 944 to provide additional functionalities to the multimedia console 103.

The multimedia console 103 may be operated as a standalone system by simply connecting the system to a television or other display. In this standalone mode, the multimedia console 103 allows one or more users to interact with the system, watch movies, or listen to music. However, with the integration of broadband connectivity made available through the network interface controller 924 or the wireless adapter 948, the multimedia console 103 may further be operated as a participant in a larger network community.

When the multimedia console 103 is powered ON, a set amount of hardware resources are reserved for system use by the multimedia console operating system. These resources may include a reservation of memory (e.g., 16 MB), CPU and GPU cycles (e.g., 5%), networking bandwidth (e.g., 8 kbs), etc. Because these resources are reserved at system boot time, the reserved resources do not exist from the application's view.

In particular, the memory reservation preferably is large enough to contain the launch kernel, concurrent system applications, and drivers. The CPU reservation is preferably constant such that if the reserved CPU usage is not used by the system applications, an idle thread will consume any unused cycles.

With regard to the GPU reservation, lightweight messages generated by the system applications (e.g., pop-ups) are displayed by using a GPU interrupt to schedule code to render pop-ups into an overlay. The amount of memory required for an overlay depends on the overlay area size and the overlay preferably scales with screen resolution. Where a full user interface is used by the concurrent system application, it is preferable to use a resolution independent of application resolution. A scaler may be used to set this resolution such that the need to change frequency and cause a TV re-sync is eliminated.

After the multimedia console 103 boots and system resources are reserved, concurrent system applications execute to provide system functionalities. The system functionalities are encapsulated in a set of system applications that execute within the reserved system resources described above. The operating system kernel identifies threads that are system application threads versus gaming application threads. The system applications are preferably scheduled to run on the CPU 901 at predetermined times and intervals in order to provide a consistent system resource view to the application. The scheduling is to minimize cache disruption for the gaming application running on the console.

When a concurrent system application requires audio, audio processing is scheduled asynchronously to the gaming application due to time sensitivity. A multimedia console application manager (described below) controls the gaming application audio level (e.g., mute, attenuate) when system applications are active.

Input devices (e.g., controllers 942(1) and 942(2)) are shared by gaming applications and system applications. The input devices are not reserved resources, but are to be switched between system applications and the gaming application such that each will have a focus of the device. The application manager preferably controls the switching of input stream, without knowledge of the gaming application's knowledge and a driver maintains state information regarding focus switches. The capture device 113 may define additional input devices for the console 103.

Figure 10:
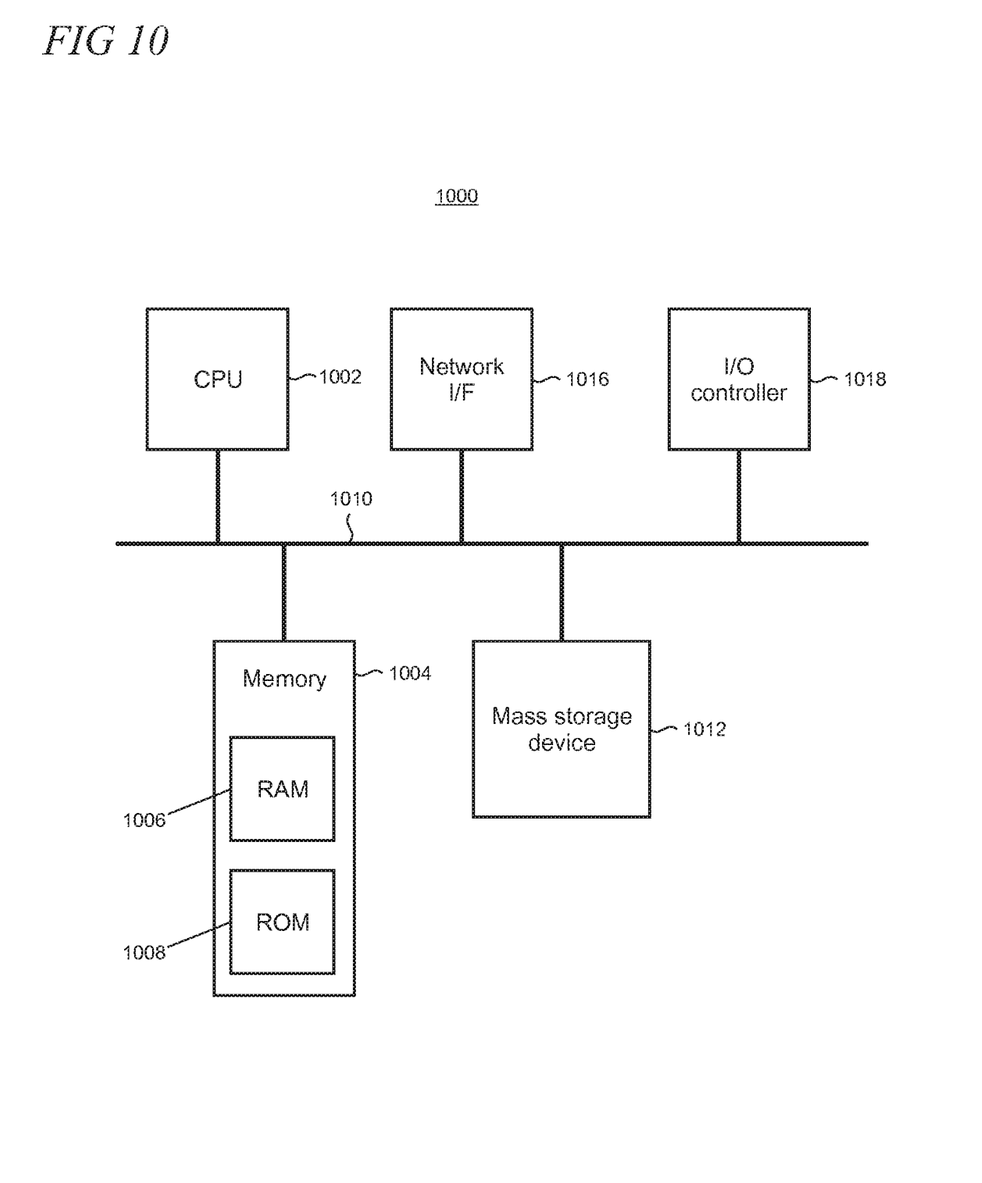
FIG. 10 shows a block diagram of an illustrative computing platform that may be used in part to implement the present optical heartrate tracking Like reference numerals indicate like elements in the drawings. Elements are not drawn to scale unless otherwise indicated.

It may be desirable and/or advantageous to enable other types of computing platforms other than the illustrative media console 103 to implement the present optical heartrate tracking in some applications. For example, optical heartrate tracking may be readily adapted to run on fixed computing platforms and mobile computing platforms that have video capture capabilities. FIG. 10 shows one illustrative architecture 1000 for a computing platform or device capable of executing the various components described herein for providing optical heartrate tracking Thus, the architecture 1000 illustrated in FIG. 10 shows an architecture that may be adapted for a server computer, mobile phone, a PDA (personal digital assistant), a smart phone, a desktop computer, a netbook computer, a tablet computer, GPS (Global Positioning System) device, gaming console, and/or a laptop computer. The architecture 1000 may be utilized to execute any aspect of the components presented herein.

The architecture 1000 illustrated in FIG. 10 includes a CPU 1002, a system memory 1004, including a RAM 1006 and a ROM 1008, and a system bus 1010 that couples the memory 1004 to the CPU 1002. A basic input/output system containing the basic routines that help to transfer information between elements within the architecture 1000, such as during startup, is stored in the ROM 1008. The architecture 1000 further includes a mass storage device 1012 for storing software code or other computer-executed code that is utilized to implement applications, the optical heartrate tracking engine, the motion tracking engine, the gesture recognition engine, the depth image processing engine, and the operating system which may configured with functionality and operations in a similar manner to those components shown in FIG. 3 and described in the accompanying text.

The mass storage device 1012 is connected to the CPU 1002 through a mass storage controller (not shown) connected to the bus 1010. The mass storage device 1012 and its associated computer-readable storage media provide non-volatile storage for the architecture 1000. Although the description of computer-readable storage media contained herein refers to a mass storage device, such as a hard disk or CD-ROM drive, it should be appreciated by those skilled in the art that computer-readable media can be any available computer storage media that can be accessed by the architecture 1000.

Although the description of computer-readable storage media contained herein refers to a mass storage device, such as a hard disk or CD-ROM drive, it should be appreciated by those skilled in the art that computer-readable storage media can be any available storage media that can be accessed by the architecture 1000.

By way of example, and not limitation, computer-readable storage media may include volatile and non-volatile, removable and non-removable media implemented in any method or technology for storage of information such as computer-readable instructions, data structures, program modules or other data. For example, computer-readable media includes, but is not limited to, RAM, ROM, EPROM (erasable programmable read only memory), EEPROM (electrically erasable programmable read only memory), Flash memory or other solid state memory technology, CD-ROM, DVDs, HD-DVD (High Definition DVD), BLU-RAY, or other optical storage, magnetic cassettes, magnetic tape, magnetic disk storage or other magnetic storage devices, or any other medium which can be used to store the desired information and which can be accessed by the architecture 1000. For purposes of this specification and the claims, the phrase "computer-readable storage medium" and variations thereof, does not include waves, signals, and/or other transitory and/or intangible communication media.

According to various embodiments, the architecture 1000 may operate in a networked environment using logical connections to remote computers through a network. The architecture 1000 may connect to the network through a network interface unit 1016 connected to the bus 1010. It should be appreciated that the network interface unit 1016 also may be utilized to connect to other types of networks and remote computer systems. The architecture 1000 also may include an input/output controller 1018 for receiving and processing input from a number of other devices, including a keyboard, mouse, or electronic stylus (not shown in FIG. 10). Similarly, the input/output controller 1018 may provide output to a display screen, a printer, or other type of output device (also not shown in FIG. 10).

It should be appreciated that the software components described herein may, when loaded into the CPU 1002 and executed, transform the CPU 1002 and the overall architecture 1000 from a general-purpose computing system into a special-purpose computing system customized to facilitate the functionality presented herein. The CPU 1002 may be constructed from any number of transistors or other discrete circuit elements, which may individually or collectively assume any number of states. More specifically, the CPU 1002 may operate as a finite-state machine, in response to executable instructions contained within the software modules disclosed herein. These computer-executable instructions may transform the CPU 1002 by specifying how the CPU 1002 transitions between states, thereby transforming the transistors or other discrete hardware elements constituting the CPU 1002.

Encoding the software modules presented herein also may transform the physical structure of the computer-readable storage media presented herein. The specific transformation of physical structure may depend on various factors, in different implementations of this description. Examples of such factors may include, but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the architecture 1000 in order to store and execute the software components presented herein. It also should be appreciated that the architecture 1000 may include other types of computing devices, including hand-held computers, embedded computer systems, smartphones, PDAs, and other types of computing devices known to those skilled in the art. It is also contemplated that the architecture 1000 may not include all of the components shown in FIG. 10, may include other components that are not explicitly shown in FIG. 10, or may utilize an architecture completely different from that shown in FIG. 10.

Based on the foregoing, it should be appreciated that technologies for providing and using optical heartrate tracking have been disclosed herein. Although the subject matter presented herein has been described in language specific to computer structural features, methodological and transformative acts, specific computing machinery, and computer-readable storage media, it is to be understood that the invention defined in the appended claims is not necessarily limited to the specific features, acts, or media described herein. Rather, the specific features, acts, and mediums are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed:

1. One or more hardware-based computer-readable memory devices not consisting of propagated signals having computer readable instructions stored thereupon that, when executed by a computer, implement:
   a face alignment and preparation pipeline configured to receive respective streams of infrared video frames and visible light video frames which include a facial image of a human subject and simultaneously process the received infrared video frames and visible light video frames to output a decomposed, frame-aligned, facial skin-only signal measurement comprising spatially-corresponding infrared light and visible light graphs that are phase-shifted so that as values in the infrared light graph are increasing, values in the spatially-corresponding visible light graph are decreasing, and vice-versa;
   a signal-finding pipeline configured to: i) receive the decomposed, frame-aligned, facial skin-only signal measurement, ii) compare the signal measurement in a current frame to a cached decomposed version of a head image in a previous frame, iii) sum up and average pixels having deltas between head images in the current frame and previous frame that trend in a consistent direction, and are within a set number of standard deviations of brightness, iv) generate a measurement of noisiness per pixel, v) apply at least one filter to the summed and averaged pixels, the filter being weighted by the noisiness measurement, vi) create a time-space representation of low-amplitude deltas in a skin-only facial image;
   a signal-extracting pipeline configured to a) apply time-space smoothing or frequency-space smoothing to the time-space representation, b) apply a discrete Fourier transform to transform the time-space representation into a frequency-space representation for each of the infrared and visible streams, c) merge the frequency-space representations weighted by graph noise level; and
   a heartrate identification pipeline configured to identify a heartrate of the human subject from the merged frequency-space representations.

2. The one or more hardware-based computer-readable memory devices of claim 1 in which the heartrate identification pipeline is configured to identify a highest peak in the merged frequency-space graphs.

3. The one or more hardware-based computer-readable memory devices of claim 2 in which the pipelines operate sequentially on a given video frame.

4. The one or more hardware-based computer-readable memory devices of claim 2 in which the pipelines operate in parallel.

5. The one or more hardware-based computer-readable memory devices of claim 2 further comprising configuring the heartrate identification pipeline to measure a noise level of the highest peak.

6. The one or more hardware-based computer-readable memory devices of claim 5 further comprising configuring the heartrate identification pipeline to bucket a location of the highest peak, weighted by the noise level into a frequency detector.

7. The one or more hardware-based computer-readable memory devices of claim 1 further comprising configuring the heartrate identification pipeline to apply a smoothing factor to nearby signals and sum the signals together.

8. The one or more hardware-based computer-readable memory devices of claim 7 further comprising configuring the heartrate identification pipeline to output a graph of the summed, smoothed signals.

9. The one or more hardware-based computer-readable memory devices of claim 8 further comprising configuring the heartrate identification pipeline to identify a heartrate signal from the graph if a peak result is above a set amplitude threshold.

* * * * *